United States Patent
Blackhurst et al.

(10) Patent No.: US 6,619,287 B2
(45) Date of Patent: Sep. 16, 2003

(54) FILTER

(75) Inventors: Michael Joseph Blackhurst, Auckland (NZ); Nina Caroline Batty, Auckland (NZ)

(73) Assignee: Fisher & Paykel Limited, Auckland (NZ)

(*) Notice: Subject to any disclaimer, the term of this patent is extended or adjusted under 35 U.S.C. 154(b) by 0 days.

(21) Appl. No.: 09/798,303

(22) Filed: Mar. 2, 2001

(65) Prior Publication Data
US 2001/0029949 A1 Oct. 18, 2001

(30) Foreign Application Priority Data
Mar. 2, 2000 (NZ) .................................. 503213

(51) Int. Cl.[7] ............................ A62B 7/10; A62B 19/00; A62B 23/02
(52) U.S. Cl. ........................... 128/205.12; 128/205.27; 128/205.28; 128/206.17; 128/201.13
(58) Field of Search ................... 128/205.12, 205.27, 128/205.28, 206.17, 201.13, 204.17, 203.26, 206.22, 911, 912; 55/359, 490.1, 495, 503, 511, 385.6, 486, 487

(56) References Cited

U.S. PATENT DOCUMENTS

| 4,062,781 A | * | 12/1977 | Strauss et al. ............... 210/446 |
| 4,148,732 A | * | 4/1979 | Burrow et al. ............... 210/232 |
| 4,727,871 A |   | 3/1988 | Smargiassi et al. |
| 4,986,904 A | * | 1/1991 | Bugar et al. ................. 210/445 |
| 5,143,060 A |   | 9/1992 | Smith |
| 5,195,527 A |   | 3/1993 | Hicks |
| 5,769,914 A | * | 6/1998 | Ku ................................ 55/320 |
| 5,983,894 A | * | 11/1999 | Fukunaga et al. ...... 128/205.12 |
| 6,129,082 A | * | 10/2000 | Leagre ................... 128/205.27 |
| 6,209,541 B1 | * | 4/2001 | Wallace .................. 128/200.24 |

FOREIGN PATENT DOCUMENTS

EP 0265163 A2 * 4/1988

* cited by examiner

Primary Examiner—Weilun Lo
Assistant Examiner—Darwin Erezo
(74) Attorney, Agent, or Firm—Trexler, Bushnell, Giangiorgi, Blackstone & Marr, Ltd.

(57) ABSTRACT

A filter for a respiratory circuit has a housing with an inlet port and an outlet port for connection to respective breathing tubes. A gases space lies between the inlet and outlet ports and gases pass across the gases space from the inlet port to the outlet port in use. A filter media spans the gases space, dividing the gases space into an inlet chamber and an outlet chamber. Gases passing from the inlet port to the outlet port pass through the filter media. A surrounding outer wall surrounds the housing apart from the inlet port and outlet port and is spaced from the wall of the housing. One or more air pockets are created between the outer wall and the housing. The air pockets insulate the housing from ambient conditions.

11 Claims, 3 Drawing Sheets

FILTER

BACKGROUND TO THE INVENTION

1. Field of the Invention

The present invention relates to filters and in particular to filters in a breathing circuit.

2. Summary of the Prior Art

Breathing circuits are well known in the art for various purposes, usually in medical applications, such as for providing breathing assistance and/or administering anaesthetics during surgical operations. Breathing circuits are also often used in providing assisted breathing during general medical care. These breathings circuits may for example extend from a ventilator or similar assisted breathing machine to a patient, and the circuit may include such auxiliary devices as in line humidifiers, carbon dioxide absorbers or antibacterial filters. These auxiliary components may be provided in the inspiratory or expiratory lines as appropriate.

U.S. Pat. No. 5,195,527, Hicks, shows an antibacterial filter for incorporation into a respiratory system, in particular in which a wall of filter media bisects a housing, being clamped between two parts forming the housing, one such part incorporating an inlet port and the other such part incorporating an outlet port such that gases flowing from the inlet port to the outlet port must pass through the antibacterial filter barrier. The filter disclosed in this publication includes flow deflectors at the entrances to the filter housing and flow directing vanes within the housing to disperse the gases flow and make effective use of the entire antibacterial filter surface. A filter of this type however has significant problems in handling a humidified gases stream, either humidified actively by incorporation of an in line humidifier in the respiratory system, or as a result of patient breathing. In particular condensation forms on the housing walls. This is exacerbated by condensation forming on the obstructions formed by the flow dispersing arrangements. Where the respiratory circuit is in use for significant periods of time condensation build up can be substantial and may pose a risk to patient health where there is any possibility of back flow to the patient. Furthermore a build up of condensation may lead to significant liquid wetting of the bacterial filter material and therefore a reduction in air permeability of the filter.

U.S. Pat. No. 4,727,871, Smargiassi et al, shows an exhalation system for connection in the exhalation path of a ventilator, in which a bacteria filter is mounted in an aluminium housing which is heated by a heating element with the purpose of reducing condensation in the bacterial filter and in other components of the system which are also mounted within the aluminium housing. This of course requires the provision of heating elements and means of controlling and supplying power to the heating elements which would together be a significant cost and which, particularly with the humid environment, have significant safety implications.

U.S. Pat. No. 5143060, Smith, shows an insulated carbon dioxide absorption system which incorporates a bacterial filter similar to that of Hicks within an insulated carbon dioxide absorption canister to utilise the heat generated in the reaction of the carbon dioxide with the granular absorbent material in warming and conditioning the respiratory gases for appropriate use with a patient. This device forms a substantial integrated component whose therefore associated costs do not lend itself to disposal, nor to use in non surgical or long term applications. With the bacterial filter disposed in an opaque housing there is the further disadvantage that detection of liquid build up, should any occur, is hindered.

SUMMARY OF THE INVENTION

It is therefore an object of the present invention to provide a bacteria filter which will at least go some way to overcoming the above disadvantages.

In a first aspect the invention may broadly be said to consist in a filter for a respiratory circuit comprising or including:

a housing having an inlet port and an outlet port for connection to respective breathing tubes and a gases space between said inlet port and said outlet port across which gases pass from said inlet port to said outlet port in use, filter media spanning said gases space to divide said gases space into an inlet chamber and an outlet chamber such that gases passing across said gases space from said inlet port to said outlet port must pass through said filter media, and, surrounding outer wall means surrounding said housing but for said inlet port and said outlet port and spaced from the wall of said housing to provide there between one or more air pockets between said outer wall means and said housing, which pockets together at least substantially surround said housing but for said inlet port and said outlet port to thereby insulate said housing (but for said inlet port and said outlet port) from ambient conditions.

In a further aspect the invention may broadly be said to consist in an insulating cover for a filter, said filter having an inlet port and an outlet port substantially coaxial therewith and spaced apart from said inlet port, and a filter media enclosing housing which first expands and then contracts as it extends between said inlet port and said outlet port, said insulating cover comprising or including a pair of cover members, each said cover member including a collar for fitting closely over one of said inlet port or said outlet port, a spacing member extending from said collar along the direction of their respective inlet or outlet port to space the collar away from the filter housing, and shell means extending to surround a respective portion of said housing, each said shell means having a periphery substantially at the broadest extent of said filter, the periphery of one said insulating cover being formed to interengage with the periphery of the other said insulating cover, such that the pair of covers may be fitted over their respective said inlet port or outlet port and brought together such that their peripheries engage, said spacing members keep the inlet port/outlet port surrounding collars spaced from said housing of said filter and said filter housing is enclosed within the insulating cover thus assembled.

In a still further aspect the invention may broadly be said to consist in a method of constructing a filter for a respiratory circuit comprising or including the steps:

1) clamping a web of filter media about its periphery between the periphery of a first housing forming part and the periphery of a second housing forming part, 2) fusing said first and second housing forming parts at their peripheries, 3) fitting a first cover forming shell over said first housing forming part such that an inlet port of said first housing part passes through an aperture in said first cover forming shell, 4) fitting a first cover forming shell over said first housing forming part such that an outlet port of said first housing part passes through an aperture in said first cover forming shell, 5) engaging said first and second cover forming shells such that said cover forming shells enclose the filter formed by the first and second housings and said web of filter media.

DETAILED DESCRIPTION

Figure 1:
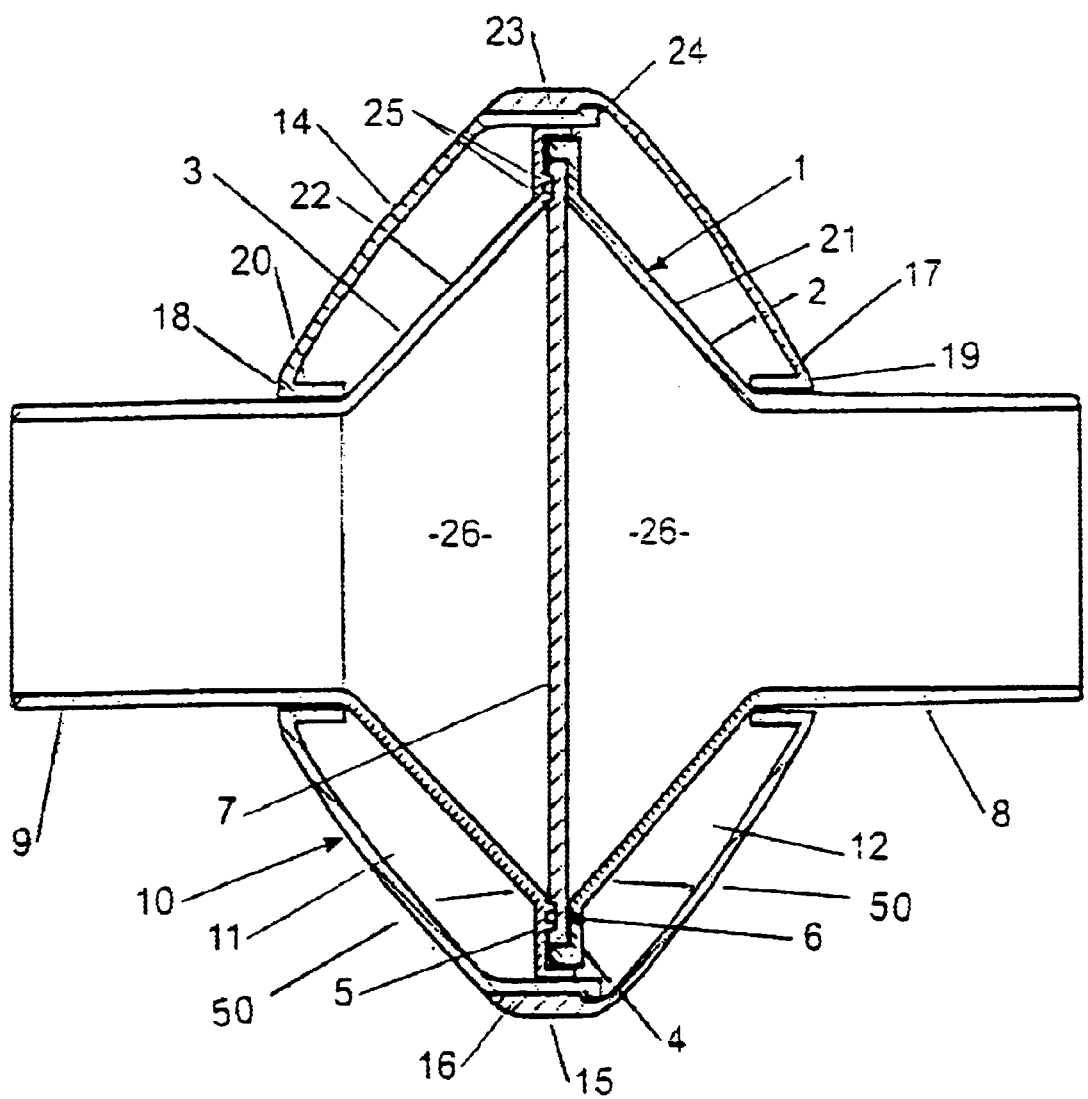
FIG. 1 shows a side elevation in cross section of a filter, including insulating cover according to the present invention, and FIGS. 2A–2D demonstrate the process of assembly of the filter of FIG. 1.

Referring to FIG. 1 the filter of the present invention has a filter housing 1 formed from a first housing part 2 and a second housing part 3. The first and second housing parts 2, 3 are joined at their respective peripheries 4, 5. The peripheries 4, 5 of said first and second parts 2, 3 clamp there between the peripheries 6 of a web 7 of filter material. The first and second housing parts 2, 3 each include one of an inlet port 8 and outlet port 9. The inlet and outlet ports are essentially indistinguishable and interchangeable. An insulating outer wall 10 is provided in the form of a cover which covers the main filter media enclosing body of the filter housing 1. The filter housing 1 and the surrounding outer wall 10 form there between a pair of closed air spaces 11, 12. These closed air spaces 11, 12 insulate the filter housing 1 from the ambient conditions outside the surrounding outer wall 10. The surrounding outer wall 10 is formed by a pair of cover sections 13, 14 which at their periphery 15, 16 have a "snap fit" connection with one another. Each cover section 13, 14 has a respective collar 17, 18 which fits over the inlet port 8 or the outlet port 9 respectively. Each collar 17, 18 has an extension 19, 20 thereof extending towards the web 7 of the filter media to abut against a face 21, 22 of the respective housing parts 2, 3 extending outwardly from the ports 8, 9 in a direction towards the web 7 of the filter media.

In viewing FIG. 1 it will be appreciated that in the form shown the filter is rotationally symmetric and so the cross section on any longitudinal plane will look like that in FIG. 1. It would of course be possible to construct the filter to have a more rectangular shape, e.g. of the web 7 of filter media and the associated peripheries 4, 5 of the housing parts 2, 3, with the wall 21, 22 merging between the rectangular shapes of the peripheries 4, 5 and the circular peripheries of the inlet and outlet ports 8, 9.

In some applications it may be preferred that the filter have more than one port on one or more of the sides of the filter media, for example, two ports on what is a ventilator side of the filter media and a single port on what is a patient side of the filter media. In such case the two ports may for example be side by side or alternatively be coaxial ports for connection to a coaxial tube or splitting connector. In a coaxial arrangement the configuration of the filter housing and the insulating cover may be simply that as shown in FIG. 1. In a side by side configuration the respective filter housing part will have a pair of ports and the respective cover section a pair of apertures or openings therethrough to fit closely over the pair of ports.

Preferably the major components of the filter, excluding the filter media, are formed from a suitable plastics material, and in particular one approved for medical uses. For example these, the first and second housing parts 2, 3 and the cover sections 13, 14, may be injection moulded from a medical grade polypropylene material. The filter media may be varied according to the intended application to include, for example antimicrobial properties or simply to be a particle filter. In this latter role the filter material may, for example, be a non woven felt of electrostatically charged polypropylene fibres, such as that marketed under the trade mark ELECTROSTAT by All Felt Incorporated. An alternative example of an appropriate filter media may be pleated paper media.

Connection between the first and second housing parts 2, 3 is preferably performed by a permanent bonding process to ensure a suitable seal between the two parts. To that purpose the first and second parts 2, 3 have overlapping flanges 24, 23 respectively and these flanges provide surfaces which may be joined by a suitable adhesive or preferably by ultrasonic welding in a known fashion. To grip the periphery 6 of the web 7 of filter media between the peripheries 4, 5 of the first and second housing parts 2, 3 a suitable ridge or ridges 25 are preferably provided on one (in this case the second housing part 3) of the housing parts 2, 3.

In use the filter will be connected in either the inspiratory or expiratory lines as appropriate between two length of a breathing circuit, preferably an insulated breathing circuit. With the enclosed space 26 within the filter being substantially insulated from the ambient conditions outside the outer wall 10 condensation forming within the filter on the filter walls will be substantially reduced. In one optional embodiment of the invention one or more apertures 50 may be provided in the walls 21 and/or 22 of the housing parts 2, 3 adjacent the periphery flanges 4, 5 thereof such that if sufficient such holes are provided any liquid gathering in the spaces 26 will flow through the apertures and into the air pockets 11, 12.

Figure 2A:
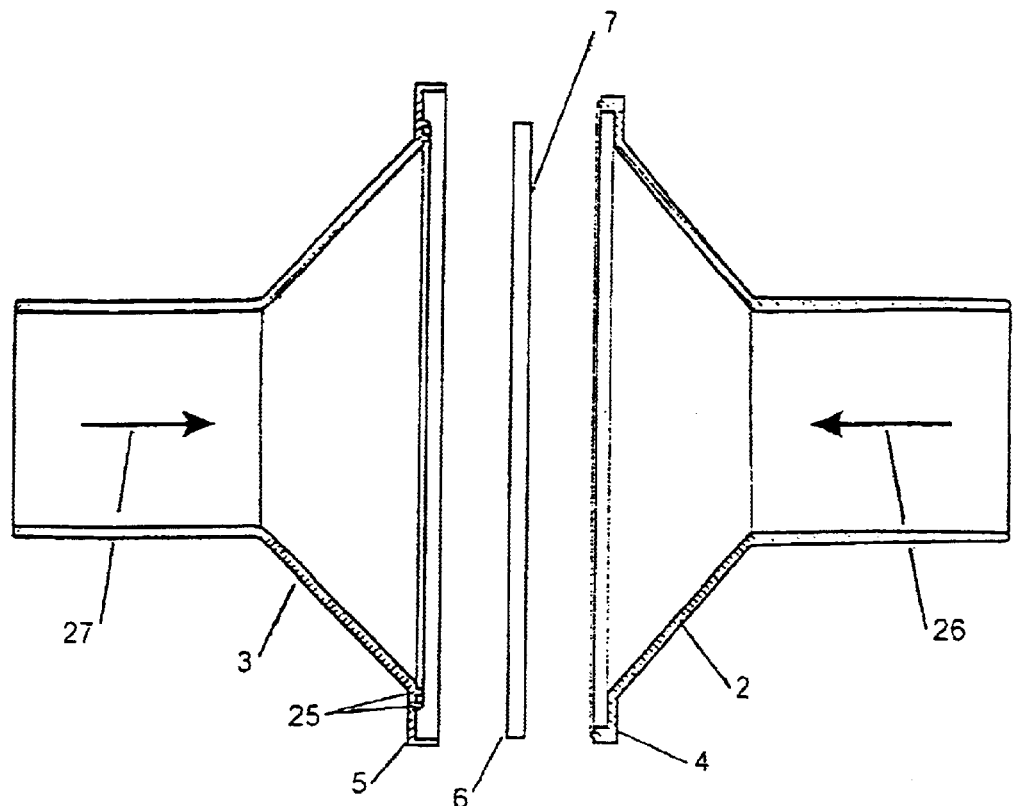
Figure 2B:
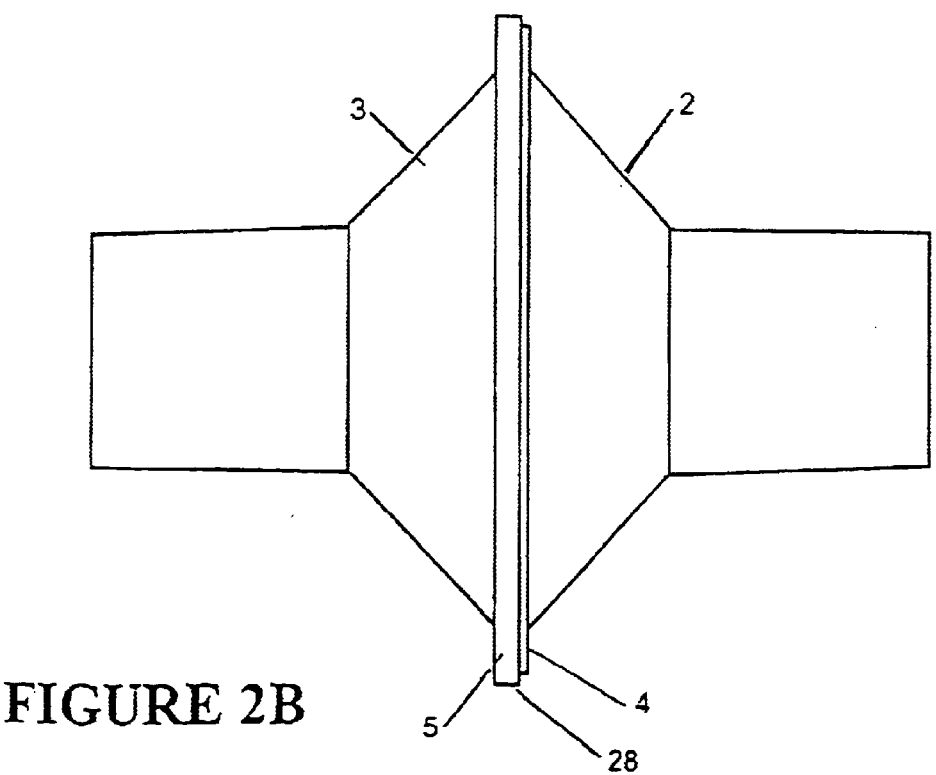

The insulated filter as provided in the present invention is furthermore of a simple construction. This construction is demonstrated with respect to FIGS. 2A to 2D. The filter involves 5 simple components being the first and second housing parts 2, 3, the web 7 of the filter media and the cover sections 13, 14 forming the outer wall. The first step of assembly is depicted in the cross sectional side elevation of FIG. 2A. The housing parts 2, 3 are brought together in the manner indicated by arrows 26, 27 to clamp the peripheries 6 of the web 7 of the filter media between the outwardly extending peripheral flanges 4, 5 of the housing parts 2, 3. Annular projecting ribs 25 on the forwardly facing surface of the peripheral flange 5 of housing part 3 grips the periphery 6 of the web 7 of filter material and squeezing same against the periphery flange 4 of housing part 2. The assembled filter housing is thus shown in the side elevation of FIG. 2B. In the condition thus shown the periphery flange 28 of the housing, formed by the periphery flanges 4, 5 is subject to ultrasonic welding to firmly and sealingly bond together the housing parts 2, 3.

Figure 2C:
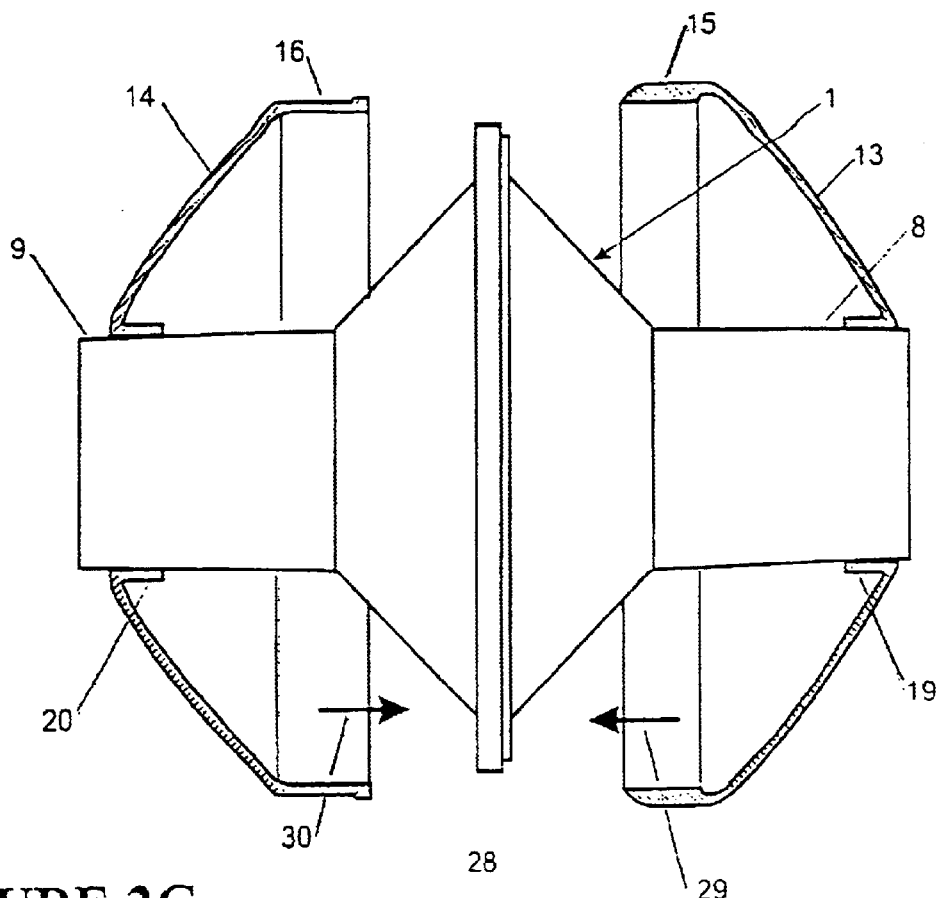

Referring then to FIG. 2C a first cover section 13 is introduced having a collar 19 thereof passing over or around the inlet port 8 of the filter housing 1. A second cover section 14 is introduced to have collar 20 thereof pass over and around outlet port 9. The first and second cover sections 13, 14 are brought together in the direction as indicated by arrows 29, 30 such that the forwardly facing peripheral flanges 15, 16 overlap and the complementary engagement surfaces formed thereon interengage to connect the cover sections 13, 14.

Figure 2D:
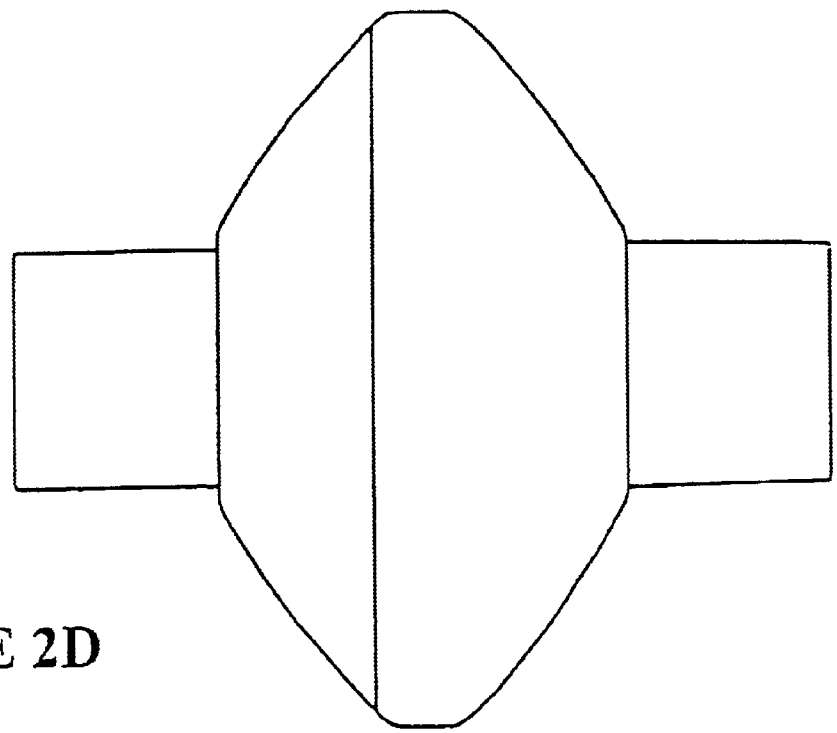

The completely assembled filter including insulating cover is depicted in the side elevation of FIG. 2D.

What we claim is:

1. A filter for a respiratory circuit comprising:
   an inlet wall defining an inlet port for connection to a breathing tube,
   an outlet wall defining an outlet port for connection to a breathing tube,
   a housing provided between said inlet wall and said outlet wall and defining a gas space between said inlet port and outlet port across which gases pass from said inlet port to said outlet port in use,
   filter media spanning said as space to divide said gas space into an inlet chamber and an outlet chamber within said housing such that gases passing across said gas space from said inlet port to said outlet port pass though said inlet chamber, said filter media and said outlet chamber, and,
   a surrounding outer wall completely surrounding said housing and spaced from said housing to provide one or more air pockets between said outer wall and said housing, to thereby insulate said housing from ambient conditions.

2. A filter as claimed in claim 1 wherein said filter media comprises a substantially planar web orientated perpendicular to a direct flow path from said inlet port to said outlet port, said web has a periphery secured to and sealed with said housing and said web is of substantially greater area than a sectional area of each of said inlet port and said outlet port, said sectional area taken parallel to said web.

3. A filter as claimed in claim 2 wherein said housing includes wall portions extending on an annular basis from around the periphery of said web to each of said inlet port and said filter media and a contracting funnel from said filter media to said outlet port.

4. A filter as claimed in claim 3 wherein said outer wall comprises first and second cover members; said first cover member having a collar fitted over said inlet wall, a periphery located annularly around or in the vicinity of said periphery of said filter media, and a wall member extending on an annular basis from said collar to said periphery to enclose there within, and be spaced apart from, said expanding funnel; said second cover member having a collar fitted over said outlet wall, a periphery located annularly around or in the vicinity of said periphery of said filter media, and a wall member extending on an annular basis from said collar to said periphery to enclose there within and be spaced apart from said contracting funnel, and
   said first and second cover members substantially sealingly connected at their said peripheries.

5. A filter as claimed in claim 4 wherein said connection at said peripheries is a snap fit connection.

6. A filter as claimed in claim 5 wherein said snap fit connection involves said cover members overlapping the other said cover member.

7. A filter as claimed in claim 5 wherein at their respective collar each said cover member has a spacing member extending towards said filter media to abut said housing to locate the respective cover members relative to said housing.

8. A filter as claimed in claim 5 wherein said housing comprises two plastic components, the first said plastic component incorporating said inlet wall and said expanding funnel, said second plastic component incorporating said outlet wall and said contracting funnel, said first and second components being connecting at their respective peripheries thereof and clamping between the peripheries thereof of the periphery of said filter media.

9. A filter as claimed in claim 8, wherein the peripheries of said first and second components of said housing are adjoined and sealed permanently to one another.

10. A filter as claimed in any one of claims 1 to 9 wherein one or more outlets are provided through said housing adjacent the periphery thereof to allow egress of condensed fluids in use into the air space between said housing and said outer wall.

11. An insulating cover for a filter, said filter having an inlet wall defining an inlet port extending in a first direction and an outlet wall defining an outlet port substantially coaxial with said inlet wall and spaced apart from said inlet wall, and a filter media enclosing housing which first expands from said inlet wall to a section of broadest extent and then contracts to said outlet wall, said insulating cover comprising:
   a pair of cover members, each said cover member including a collar for fitting closely over one of said inlet wall or said outlet wall, a spacing member extending from said collar for extending along an inlet or outlet wall over which the collar is fitted to space the collar away from the filter media enclosing housing, and a shell extending from said collar to a periphery sufficient to surround the section of said filter of broadest extent;
   such that in assembly to the filter, each of the pair of cover members are fitted over their respective inlet wall or outlet wall and brought together such that the peripheries of their respective shells engage with the surrounding collars spaced from the filter media enclosing housing of the filter by the spacing members and the filter media enclosing housing is completely enclosed within the insulating cover.

* * * * *

UNITED STATES PATENT AND TRADEMARK OFFICE
CERTIFICATE OF CORRECTION

PATENT NO.    : 6,619,287 B2                                              Page 1 of 1
DATED         : September 16, 2003
INVENTOR(S)   : Michael Joseph Blackhurst and Nina Caroline Batty It is certified that error appears in the above-identified patent and that said Letters Patent is hereby corrected as shown below:

<u>Column 5,</u>
Line 11, "as" should be -- gas --

Signed and Sealed this

Tenth Day of February, 2004

JON W. DUDAS
*Acting Director of the United States Patent and Trademark Office*